(12) United States Patent
Segal

(10) Patent No.: US 6,430,830 B1
(45) Date of Patent: Aug. 13, 2002

(54) DENTAL MEASURING DEVICE

(76) Inventor: Alan Julian Segal, 13 Park Avenue, Hale, Cheshire (GB), WA1 59DL ( * ) Notice: Subject to any disclaimer, the term of this patent is extended or adjusted under 35 U.S.C. 154(b) by 45 days.

(21) Appl. No.: 09/688,421

(22) Filed: Oct. 16, 2000

(30) Foreign Application Priority Data

Oct. 16, 1999 (GB) .............................................. 9924407

(51) Int. Cl.⁷ .......................... G01B 3/38; A61C 19/04
(52) U.S. Cl. ........................................ 33/513; 33/806
(58) Field of Search .......................... 33/511, 512, 513, 33/514, 1 BB, 783, 784, 792, 793, 794, 795, 796, 802, 806, 809, 810, 811, 812, 813, 826, 831, 402

(56) References Cited

U.S. PATENT DOCUMENTS

| | | | | |
|---|---|---|---|---|
| 618,888 A | * | 7/1899 | Linn | 33/783 |
| 783,804 A | * | 2/1905 | Smith | 33/514 |
| 878,507 A | * | 2/1908 | Coghlan | 33/402 |
| 1,321,567 A | * | 11/1919 | Spindler | 33/812 |
| 3,041,732 A | * | 7/1962 | Christner | 33/810 |
| 3,835,544 A | * | 9/1974 | Schneider | 33/147 J |
| 4,106,204 A | * | 8/1978 | Schader | 33/147 T |
| 4,106,205 A | * | 8/1978 | Wiederkehr | 33/174 E |
| 4,455,753 A | * | 6/1984 | Keyes | 33/143 E |
| 4,843,720 A | * | 7/1989 | Kim | 33/812 |
| 4,938,230 A | * | 7/1990 | Machek et al. | 128/777 |
| 5,483,751 A | * | 1/1996 | Kodato | 33/811 |
| 5,584,125 A | * | 12/1996 | Prete | 33/501.45 |
| 6,205,673 B1 | * | 3/2001 | Larsen et al. | 33/810 |

FOREIGN PATENT DOCUMENTS

FR    1107136    *   8/1955   ................. 33/810

* cited by examiner

Primary Examiner—Diego Gutierrez
Assistant Examiner—Tania Courson
(74) Attorney, Agent, or Firm—Hollander Law Firm, P.L.C.

(57) ABSTRACT

A dental measuring device can be used to measure the separation of reference positions on a patient's upper and lower jaws to assist in the construction of dentures. The device has two elements which slide longitudinally relative to each other with a pointer on one and a scale on the other. The elements have projecting arms. The sliding elements can be reversed so that in one position the arms point in the same direction for measuring the separation of specific points on the patient's nose and chin, and in a second position the arms point in opposite directions for positioning beneath the patient's nose and chin.

19 Claims, 2 Drawing Sheets

DENTAL MEASURING DEVICE

Figure 1:
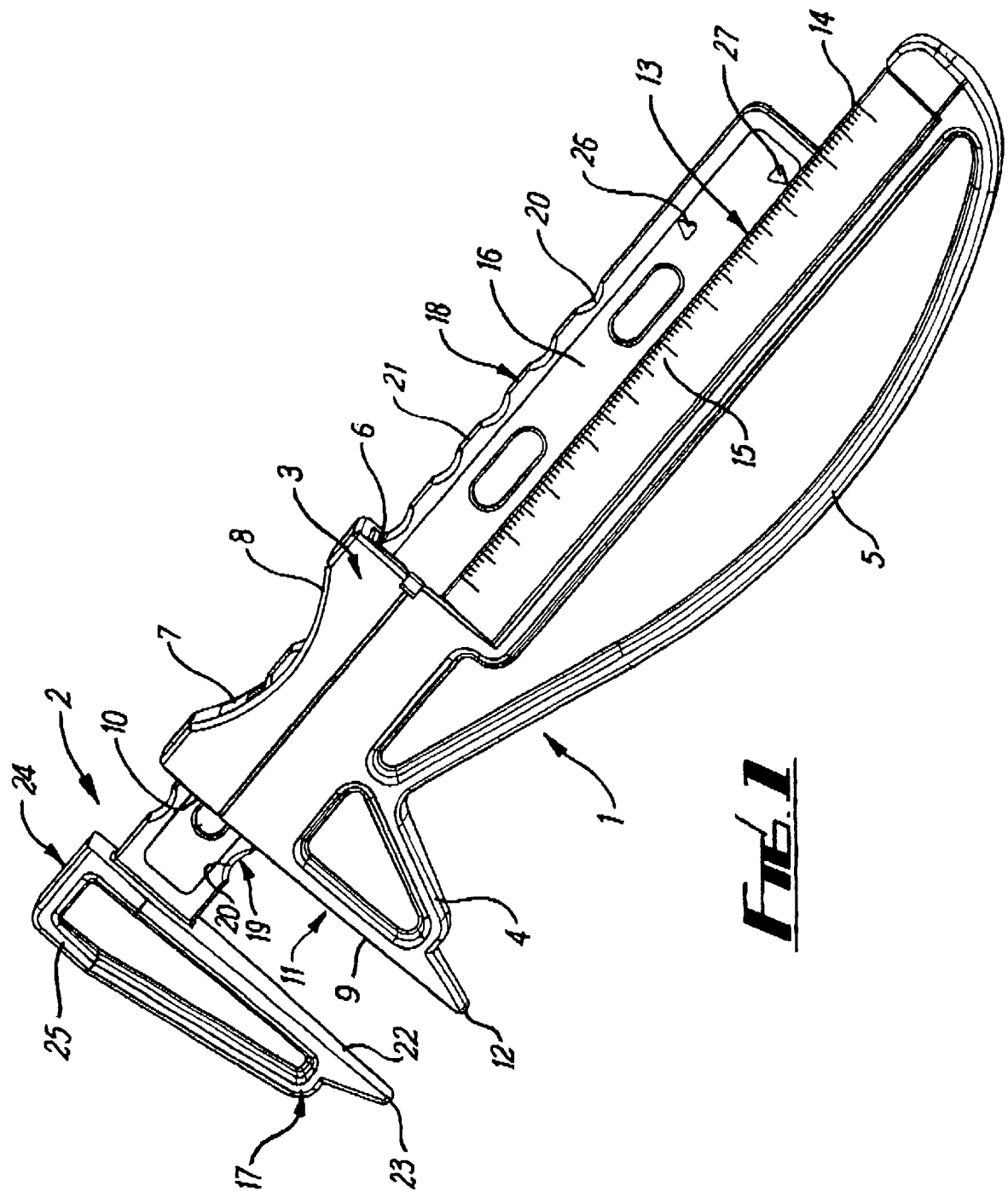

This invention relates to a dental measuring device, or bite gauge, for measuring the separation of reference positions relative to a patient's upper and lower jaws.

To facilitate construction of comfortably fitting dentures or other fixed or movable dental prosthetics it is desirable to know the natural vertical separation at rest, or in a relaxed condition, of a patient's upper and lower and lower jaws.

There are however, problems associated with the selection of appropriate reference points and with the accurate measurement of the separation of these points in so far as the selected points may lack precise definition and their vertical separation depends on the state of relaxation of the patient.

One known technique ('nose point to chin point') involves the use of conventional measuring tools, such as dividers or a micrometer gauge, applied between an upper point on the tip of the patient's nose and a lower point on the patient's chin. These are arbitrary points. It is usual to determine the spacing of the points in a rest position and also when the patient's teeth are biting together. It is considered optimum to have a differential between the two readings of say 2–3 mm.

It has also been proposed to measure the distance between an ear and adjacent eye, specifically between the patient's external auditory meatus and the adjacent lateral border of the ocular orbit, on the assumption that this bears a fixed relationship to a vertical separation of that patient's upper and lower jaws. This assumption is however not necessarily correct in all cases and the measuring technique can be inconvenient or undesirable since it involves applying a measuring tool in close proximity to the patient's eye.

Another known technique ('under nose to under chin') uses a micrometer gauge having one of its measuring arms reversed so as to point in the opposite direction to the other arm. One arm, which is fixed at the end of a calibrated elongate member, is positioned under the patient's nose (nasal spine) and the other arm, which is slidable along the member, is position beneath the chin (under mandible). The slidable arm is fixed in an adjusted position on the member with a screw, and the separation of the arms can be measured along the member. This technique, like the above nose point to chin point technique, is used to give readings at rest and biting positions.

The 'nose point to chin point' and 'under nose to under chin' techniques are both commonly used. The former technique only provides a reading of the separation of the two arbitrarily selected points. The latter technique may not always provide reproducible readings in so far as the reading is dependent on the compression force applied to the patient's tissues when the readings are taken, Accordingly it is usual for a decision to be taken as to which technique is preferred for each patient, dependent on factors such as the presence of any beard, angle of bone structure, and chin fat.

However, an instrument suitable for use with one technique may not be readily suitable for use with the other technique. Thus, a conventional micrometer gauge which is calibrated to give a reading of the separation of inner confronting surfaces of its arms when they are pointing in the same direction is suitable for use in the nose point to chin point technique but may not be suitable for use in the under nose to under chin technique since, with the reversed use of the gauge it is the separation of the outer surface of the under-nose arm and inner surface of the under-chin arm which is required. Also, with the reversed use of the gauge the usual scale and pointer will no longer be in juxtaposition. The desired measurement can not therefore be read off quickly and conveniently.

An object of the present invention is to provide a dental measuring device which is simple and convenient to use in both 'nose point to chin point' and 'under nose to under chin' techniques, and with which accurate, reproducible measurements can be readily established for both such techniques.

According to the invention therefore there is provided a dental measuring device comprising a pair of measuring elements adapted for interconnection by a guide structure so as to be movable towards and away from each other along an axis, and a measurement indicating means operable to provide a readable indication of the separation of the measuring elements along the said axis, wherein the elements are adapted for interconnection in two modes, whereby in one mode they extend in different directions for positioning of contact surfaces thereof respectively under the nose and chin of a patient, and in a second mode they extend in a common direction for location relative to reference points on the nose and chin of a patient, and wherein the measurement indicating means is operable to provide said readable indication pertaining to the separation of said measuring elements in each said mode.

With this arrangement, the device can be used to give accurate, reproducible measurements for both nose point to chin point and under nose to under chin techniques.

The device is therefore a versatile, 'all purpose' instrument, and the device can be used for purposes additional to the above techniques e.g. for measuring distances on models or dentures, measuring the distance between teeth, such as intercanine distance, measuring width of teeth etc.

In the said one mode, the measuring elements are preferably directed in opposite directions, particularly diametrically opposite directions. The invention is however not restricted to this and other dispositions may also be possible e.g. with the measuring elements transversely, particularly perpendicularly, to each other.

In the said second mode, the measuring elements preferably extend in the same direction particularly in the manner of a conventional micrometer.

Adaption of the device for selection of the modes is preferably effected by selective interfitting or positional adjustment of the measuring elements relative to each other e.g. by reversal of one element relative to the other.

The measurement indicating means is appropriately adaptable so as to provide a readable indication in each mode.

Such adaptation of the measurement indicating means may be effected by selective positional adjustment or selective substitution of parts of the measurement indicating means.

The measurement indicating means may have parts comprising at least one elongate calibrated scale and at least one pointer whereby the measurement indication is established by the location of the pointer along the scale. There may be two or more pointers and/or two or more scales so that in each mode there is a respective arrangement of a juxtaposed pointer and scale to ensure presentation of readily readable measurement indications corresponding to the respective mode.

Thus, for example, there may be pointers at different longitudinal positions relative to the scale, e.g. corresponding to the difference between measurement of the separation of the said contact surfaces in the said one mode and the measurement of the separation of tips, or inner confronting faces of the measuring elements in the said other mode.

The measuring elements are preferably rigid elongate arms which have free ends and which may be tapered towards such ends. In the case where the arms can be arranged in a mode in which they extend in the same direction, the free ends, in such mode, may be level with each other, and preferably the arms are of the same length. Preferably also the elements extend along respective axes which are parallel to each other.

Preferably the elements are movable relative to each other along a straight axis to which the elements extend perpendicularly.

The guide structure for guiding relative movement of the measuring elements preferably comprises an elongate member slidable through a sleeve, the measuring elements being fixed respectively relative to the member and the sleeve. Other guiding arrangements are however also possible.

Most preferably the guide structure is such as to ensure maintenance of relative angular dispositions of the said contact surfaces of the elements during adjustment movement. Preferably also, a releasable retention device is provided to hold the elements in adjusted positions. The retention device may comprise a frictional interfit, although a ratchet arrangement, or a locking screw or any other suitable device may also be used.

The measurement device may also include a hand grip, or handle, fixed relative to one of the measuring elements to facilitate holding of the device whilst permitting adjustment of the other of the elements. Suitable, the hand grip or handle may be an elongate structure which may be fixed to the aforesaid sleeve.

Where the measurement indicating means comprises a scale and pointer as aforesaid, the scale may be fixed relative to the said sleeve e.g. on the aforesaid handle or hand grip, and the pointer may be provided on the elongate member which is slidable within the sleeve.

Where the elongate member is reversible within the sleeve for adaptation between the different modes, there may be different pointers on opposite sides of the elongate member for adaptation of the measurement indicating means to correspond to the different modes.

Figure 2:
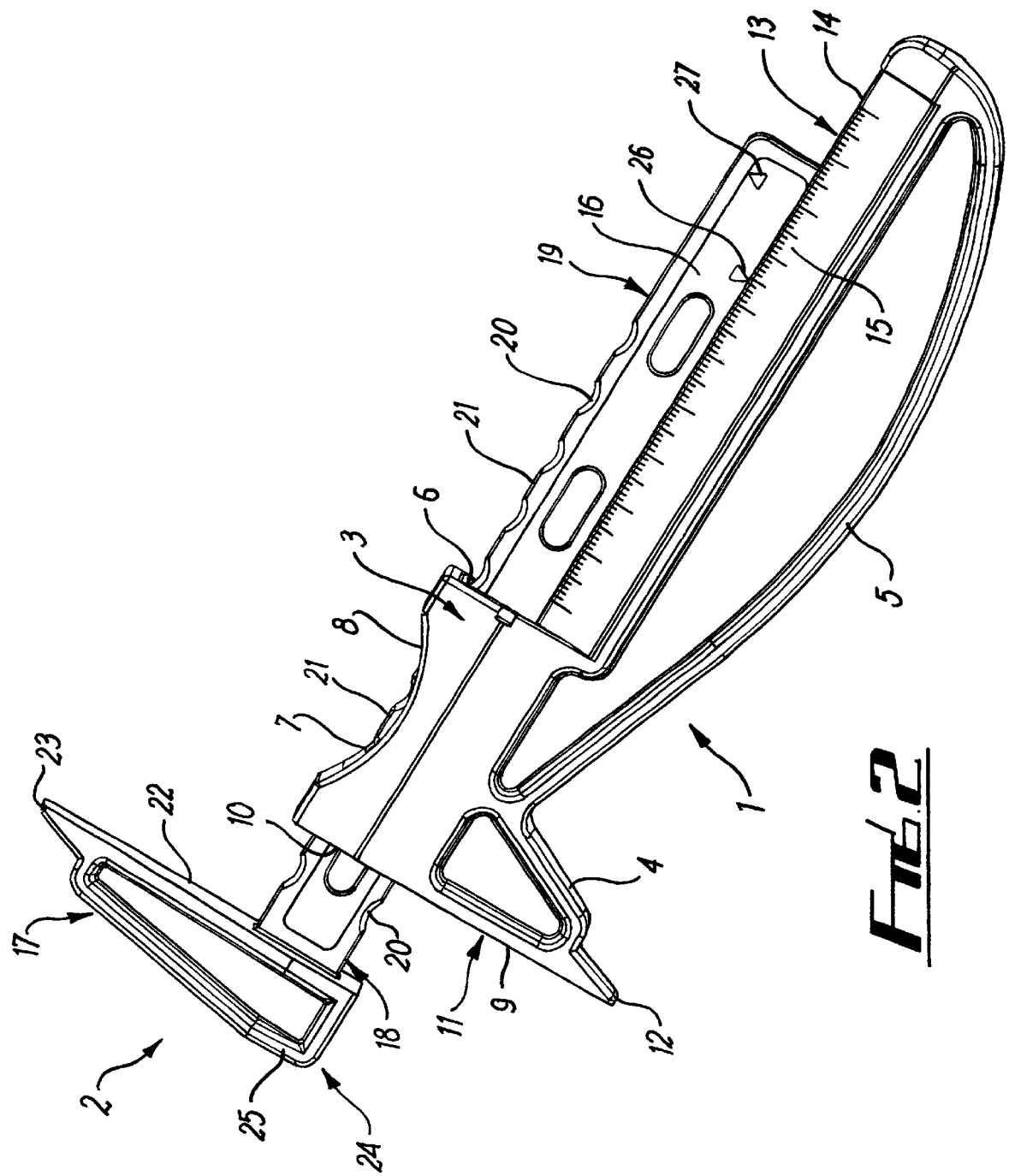

The invention will be described further by way of example only and with reference to the accompanying drawings in which FIG. 1 is a perspective view of one form of a measuring device according to the invention in one mode of use; and FIG. 2 is a view similar to FIG. 1 in an alternative mode of use.

The device shown in FIG. 1 has two interfitting parts 1, 2.

One such part 1 is a one-piece plastics moulding having a sleeve structure 3 with an arm 4 projecting at one side from a top end region of the sleeve structure 3, and an elongate shaped handle structure 5 projecting, on the same side as the arm 4 from the bottom end region of the sleeve structure 3.

The arm 4, sleeve structure 3 and handle structure 5 are of generally flat construction, that is, they have opposite flat faces and are generally of narrow rectangular cross-section The sleeve structure 3 has a narrow through-channel 6 of rectangular cross-section having a straight longitudinal axis. This channel 6 communicates with a slot-shaped aperture 7 through one side edge of the sleeve structure 3 within a central concave arcuately-curved recessed portion 8 of such side edge. The sleeve structure 3 has planar end edges perpendicular to the channel axis.

The arm 4 extends at right angles to the axis of the through channel 6 of the sleeve structure 3 and has a flat top edge 9 coplanar with the top end edge 10 of the sleeve structure 3 which edges 9, 10 define an upwardly directed planer contact face 11. The arm 4 tapers away from the sleeve structure 3 to a small-dimension rounded tip 12.

The handle structure 5 extends longitudinally beyond the bottom end edge of the sleeve structure 3 and has a straight edge 1 3, on the opposite side of the handle structure 5 to the arm 4, which edge 13 has an open channel 14 along its length and is parallel to the longitudinal axis of the through-channel 6 of the sleeve structure 3. This edge 13 overlaps the through channel 6 of the sleeve structure 3 whereby the through channel 6 and the open channel 14 are in communication with each other and the base of the open channel 14 and the inner surface of the adjacent side edge of the through channel 6 form a continuous flat guide surface.

On at least one face of the handle structure 5 there is a permanently etched a calibrated scale 15 adjacent to the edge 13.

The other part 2 of the device shown in FIG. 1 is a one-piece moulded plastics structure which comprises an elongate generally flat member 16 having an arm 17 projecting at right angles at a top end.

The member 16 has opposite long edges 18, 19 which extend generally parallel to the longitudinal axis of the member 16.

There are regularly spaced concave arcuately-curved recesses 20 along each edge 18, 19, the recesses 20 on one edge 18 being respectively aligned with the recesses 20 on the opposite edge 19. Projections 21 are defined between the recesses 20, The arm 17 has a flat bottom edge 22 at right angles to the axis of the member 16 and the arm 17 tapers away from the edge 19 of the member 16 to a small-dimensioned rounded tip 23. The arm 17 has a rear end part 24 which extends slightly beyond the edge 18 of the member 1 6 and has a top edge 25 which defines a flat contact face parallel to the contact face 11.

The member 16 has at least one pair of opposite pointers 26, 27, respectively adjacent to the two long edges 18, 19 marked or moulded thereon. There may be a respective pair of opposite pointers on each face of the member 16, or alternatively there may be only one pair of pointers in which case the pointers are disposed respectively on opposite faces of the member 16. The drawings show pairs of pointers on both faces.

As shown in FIG. 1, the member 16 can be inserted into the through channel 6 of the sleeve structure 3 and the arm 17 can be guided towards and away from the arm 4 by sliding the member 16 through the through channel 6 and along the open channel 14. The arrangement is such that, in the fully inserted position of the member 16 the flat bottom edge 22 of the arm 17 lies on and is coextensive with the planar contact surface 11 of the arm 4 and the sleeve structure 3.

The member 16 is a close fit within the channels 6, 14 so that it is guided to slide easily but with little play.

The member 16 has a rectangular cross-section which is of slightly smaller dimensions than the through channel 6 and a moulded plastic insert is provided within the channel 6 to achieve the required guided close fit with easy sliding The insert may provide sufficient friction to ensure that the member 16 is retained in a selected position or, alternatively a catch or locking device may be incorporated for this purpose.

The projecting portions 21 of the long edge 18 of the member 16 project through the side aperture 7 in the sleeve structure 3.

The device can be gripped in one hand with a person's fingers wrapped around the shaped handle structure 5 and the person's thumb on the projecting portions 21 of the long edge 18 within the recess 8, whereby the member 16 can be conveniently adjusted up or down with the person's thumb.

The device as shown in FIG. 1 can be used in conventional manner to measure the separation of two points on a patient's face by adjusting the separation of the arms 4, 17 so that the two tips 12, 23 contact the two points. The separation can then be read off on the calibrated scale 15 by noting the positioning of the adjacent point 27, the scale 15 being calibrated with regard to the position of the pointer 27 in relation to a zero separation at which the confronting faces of the two arms, i.e. the edge 22 of the arm 17 and the face 11 of the arm 4 contact each other.

As shown in FIG. 2, the device can also be used in a reversed mode. The member 16 is removed, rotated about its axis through 180° and reinserted so that the arm 17 is directed in the opposite direction to the arm 4.

In conventional manner, the contact face 11 of the arm 4 can be positioned under a patient's chin with the top contact face 25 of the back end part 24 of the arm 17 under the patient's nose to measure the separation of these two parts of the patient's face.

In this case, the separation can be read off on the calibrated scale 15 by noting the position of the pointer 26 which is now adjacent to the scale 15. This pointer 26 is spaced longitudinally from the pointer 27 by a distance equal to the spacing of the top face 25 and the bottom edge 22 of the arm 17 to compensate for the reversed mode of the device.

With the arrangement described, the device can be conveniently used to make a point-to-point measurement and also to measure the under-chin to under-nose separation. In each case, the measurement is directly read off by observing the positioning of the appropriate pointer 26 or 27 on the scale 15.

In the case where there is a respective scale on each face, and corresponding two pairs of pointers, the reading can be made from either face of the handle structure.

The device is simple and convenient to use and, being made with appropriately shaped one piece plastics mouldings can be fully autoclavable, it can be strong and lightweight and can be comfortable for the user and patient.

It is of course to be understood that the invention is not intended to be restricted to the details of the above embodiment which are described by way of example only.

What is claimed is:

1. A dental measuring device comprising a pair of measuring elements interconnected by a guide structure so as to be movable towards and away from each other along an axis, and a measurement indicating means operable to provide a readable indication of the separation of the measuring elements along the said axis, wherein the elements are adapted for interconnection in two modes, whereby in one mode they extend in different directions from each other for positioning of contact contact surfaces thereof respectively under the nose-and chin of a patient, and in a second mode they extend in a common direction for location relative to reference points on the nose and chin of a patient and wherein the measurement indicating means is operable to provide said readable indication pertaining to the separation of said measuring elements in each said mode.

2. A measuring device according to claim 1 wherein in the said one mode the measuring elements are directed in opposite directions from each other.

3. A measuring device according to claim 1 wherein adaptation of the device for selection of the said modes is effected by reversal of one element relative to the other.

4. A measuring device according to claim 1 wherein the measurement indicating means is adaptable so as to provide a readable indication in each mode.

5. A measuring device according to claim 4 wherein said adaptation of the measurement indicating means is effected by selective positional adjustment of parts of the measurement indicating means.

6. A measuring device according to claim 1 wherein the measurement indicating means has parts comprising at least one elongate calibrated scale and at least one pointer whereby the measurement indication is established by the location of the pointer along the scale.

7. A measuring device according to claim 6 wherein said at least one pointer comprises at different longitudinal positions relative to the scale corresponding to the difference between measurement of the separation of the said measuring elements in each said mode.

8. A measuring device according to claim 6 wherein the guide structure for guiding relative movement of the measuring elements comprises an elongate member slidable through a sleeve, the measuring elements being fixed respectively relative to the member and the sleeve.

9. A measuring device according to claim 8 further including a handgrip or handle fixed relative to one of the measuring elements to facilitate holding of the device whilst permitting adjustment of the other of the elements.

10. A measuring device according to claim 9 wherein the scale is fixed to the handgrip or handle.

11. A measuring device according to claim 7 wherein the pointer is provided on the elongate member which is slidable within the sleeve.

12. A measuring device according to claim 9 wherein the handgrip or handle is fixed to the sleeve.

13. A measuring device according to claim 8 wherein the scale is fixed relative to the sleeve.

14. A measuring device according to claim 8 wherein said at least one pointer comprises pointers on opposite sides of the elongate member for adaptation of the measurement indicating means to correspond to the different modes.

15. A measuring device according to claim 1 wherein the measuring elements are rigid elongate arms with free ends, the arms being tapered towards such ends.

16. A measuring device according to claim 1 wherein the measuring elements are movable relative to each other along a straight axis to which the elements extend perpendicularly.

17. A measuring device according to claim 1 wherein the guide structure is such as to ensure maintenance of relative angular dispositions of the said contract surfaces of the elements during adjustment movement.

18. A measuring device according to claim 1 wherein a releasable retention device is provided to hold the elements in adjusted positions.

19. A measuring device according to claim 18 wherein the retention device comprises a frictional interfit.

* * * * *